United States Patent [19]
Schmid

[11] Patent Number: 5,936,139
[45] Date of Patent: Aug. 10, 1999

[54] CYCLOPROPANE FATTY ACID EXPRESSION IN PLANTS

[76] Inventor: Katherine M. Schmid, 4644 Rookwood Ave., Indianapolis, Ind. 46208

[21] Appl. No.: 08/844,305

[22] Filed: Apr. 10, 1997

Related U.S. Application Data

[63] Continuation of application No. 08/275,867, Jul. 15, 1994, abandoned.

[51] Int. Cl.$^6$ .............................. A01H 5/00; C12N 5/04; C12N 15/82
[52] U.S. Cl. ........................ 800/281; 435/69.1; 435/419; 536/23.7
[58] Field of Search .............................. 435/69.1, 320.1, 435/419; 536/23.7; 800/205, DIG. 14, DIG. 17, DIG. 23, DIG. 26, DIG. 43, DIG. 63, 298, 281

[56] References Cited

U.S. PATENT DOCUMENTS 5,015,580   5/1991   Christou et al. ..................... 435/172.3

FOREIGN PATENT DOCUMENTS 9113980   9/1991   WIPO .
9218634  10/1992   WIPO .
WO 92/18634  10/1992   WIPO .

OTHER PUBLICATIONS

Grogan et al. Cloning and manipulation of the *Escherichia coli* cyclopropane fatty acid synthase gene: physiological aspects of enzyme overproduction. Journal of Bacteriology. 158(1):286–295, Apr. 1984.

Wang et al. Cyclopropane fatty acid synthase of *Escherichia coli*: deduced amino acid sequence, purification, studies of the enzyme active site. Biochemistry. 31(45):11020–11028, 1992.

Christie, Wm., Cyclopropane and Cyclopropane Fatty Acids, (1970) pp. 1–49 Topics in Lipid Chemistry.

Christie, et al., Mass Spectrometry of Lipids. 1. Cyclopropane Fatty Acid Esters, Lipids vol. 1, No. 3, pp. 176–182 (1966).

Battey J.F., et al., "Genetic Engineering for Plant Oils: Potential and Limitations" Tibtech, vol. 7 (May 1989) pp. 122–125.

Mangold, H., et al., "Biosynthesis of Cyclic Fatty Acids" (1980) The Biochemistry of Plants, vol. 4, 647–663.

Horsch, et al., "A Simple and General Method for Transferring Genes into Plants", (1985) Science, vol. 227, pp. 1229–1231.

Hooykaas, Paul J.J., "Transformation of Plant Cells via Agrobacterium" (1989) Plant Molecular Biology 13: 327–336.

An, G., "Binary Ti Vectors for Plant Transformation and Promoter Analysis" (1987) Methods in Enzymology, vol. 153, 292–305.

Hoekema, et al., "A Binary Plant Vector Strategy Based on Separation of vir– and T–region of the *Agrobacterium Tumefaciens* Ti–Plasmid", Nature, vol. 303, (1983) pp. 179–180.

Gaydou, et al., "Cyclopropanoic Fatty Acids of Litchi (*Litchi chinensis*) Seed Oil. A Reinvestigation" J. Agric. Food Chem. (1993) 41: 886–890.

Vickery, J.R., "The Fatty Acid Composition of Seed Oils from Ten Plant Families with Particular Reference to Cyclopropane and Dihydrosterculic Acids" (1980) J. Am. Oil Chem. Soc. 57: 87–91.

Schmid, et al., "Distribution of Cyclopropenoid Fatty Acids in Malvaceous Plant Parts" (1988) Phytochemistry, vol. 27, No. 9 pp. 2831–2834.

Jie, et al., "*Litchi Sinensis* Seed Oil: A Source of Dihydrosterculic Acid and cis–9, 10–Methylenehexadecanoic Acid" (1977) J.C.S. Chem. Comm. p. 78.

Chung, et al., "Cyclopropane Fatty Acid Synthetase: Partial Purification and Properties" (1964) Biochemistry vol. 3, No. 7, 967–974.

Grogan, et al., "Cloning and Manipulation of the *Escherichia coli* Cyclopropane Fatty Acid Synthase Gene: Physiological Aspects of Enzyme Overproduction" (1984) J. of Bacteriology vol. 158, No. 1, 286–295.

Law, J., "Biosynthesis of Cyclopropane Rings" (1971) ACCTS Chem. Res. vol. 4, pp. 199–203.

Marinari, et al., "Specificity of Cyclopropane Fatty Acid Synthesis in *Escherichia coli*. Utilization of Isomers of Monounsaturated Fatty Acids" (1974) Biochemistry 13: 1978–1982.

Ohlrogge, et al., "Positional Specificity of Cyclopropane Ring Formation From CIS–octadecenoic Acid Isomers in *Escherichia Coli*" (1976) Biochimica et Biophysica Acta, 431, pp. 257–267.

Wang, et al., "The Growth Phase–Dependent Synthesis of Cyclopropane Fatty Acids in *Escherichia coli* is the Result of an RpoS(KatF)–dependent promoter plus Enzyme Instability" (1994) Molecular Microbiology 11(6) pp. 1009–1017.

(List continued on next page.)

*Primary Examiner*—Elizabeth F. McElwain
*Attorney, Agent, or Firm*—Saliwanchik, Lloyd & Saliwanchik

[57] ABSTRACT

Pants are transformed with a bacterial cyclopropane fatty acid synthase gene to produce lipids containing cyclopropane fatty acids. Using this technology dihydrosterculate is produced in oilseed crops such as rape.

20 Claims, 3 Drawing Sheets

OTHER PUBLICATIONS

Wang, et al., "Cyclopropane Fatty Acid Synthase of *Escherichia coli:* Deduced Amino Acid Sequence, Purification, and Studies of the Enzyme Active Site" (1992) Biochemistry, vol. 31, pp. 11020–11028.

Taylor, et al., "Cyclopropane Fatty Acid Synthase of *Escherichia coli.* Stabilization, Purification, and Interaction with Phospholipid Vesicles" (1979) Biochemistry, vol. 18, No. 15, pp. 3291–3300.

Grogan, et al., "Characterization of *Escherichia coli* Mutants Completely Defective in Synthesis of Cyclopropane Fatty Acids" (1986) J. Bacteriology, vol. 166, No. 3, pp. 872–877.

Sengupta–Gopalan, et al., "Developmentally regulated expression of the bean beta–Phaseolin gene in tobacco seed" Proc. Natl. Acad. Sci. USA, vol. 82 (1985), pp. 3320–3324.

Nunberg, et al., "Developmental & Hormonal Regulation of Sunflower Helianthinin Genes: Proximal Promoter Sequences Confer Regionalized Seed Expression," The Plant Cell, vol. 6 (1994), pp. 473–486.

Bustos, et al., "Positive and negative cis–acting DNA Domains are required for spatial and temporal regulation of gene expression by a seed storage protein promoter," The EMBO Journal, vol. 10 (1991), pp. 1469–1479.

Ohlrogge, "Design of New Plant Products: Engineering of Fatty Acid Metabolism," Plant Physiology, vol. 104 (1994), pp. 821–826.

Bohannon, et al., "Cyclopropene Fatty Acids of Selected Seed Oils from Bombacaceae, Malvaceae, and Sterculiaceae," Lipids, vol. 13 (1978), pp. 270–273.

Yano, et al., "The Biosynthesis of Cyclopropane and Cyclopropene Fatty Acids in Higher Plants (Malvaceae)," Lipids, vol. 7 (1972), pp. 35–45.

Stayton, et al., "High–level, Seed–specific Expression of Foreign Coding Sequences in *Brassica napus,*" Aust. J. Plant Physiol., vol. 18 (1991), pp. 507–517.

Willmitzer 1993 In Biotechnology, vol. 2. Genetic Fundamentals & Genetic Engineering, 2nd Edition, Rehmetal (eds), VCH publisher, pp. 627–659.

Kahl et al 1993 ibid pp. 547–625.

Chesh et al. 1995 In Plant Lipid Metabolism, Kader et al (eds), Kluwer Academic Publishes, Netherlands, pp. 570–572.

Yuan et al 1995 Proc Natl Acad Sci USA 92: 6630–6634.

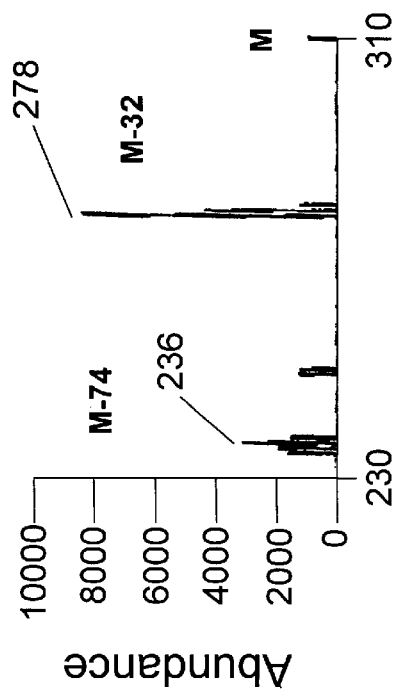
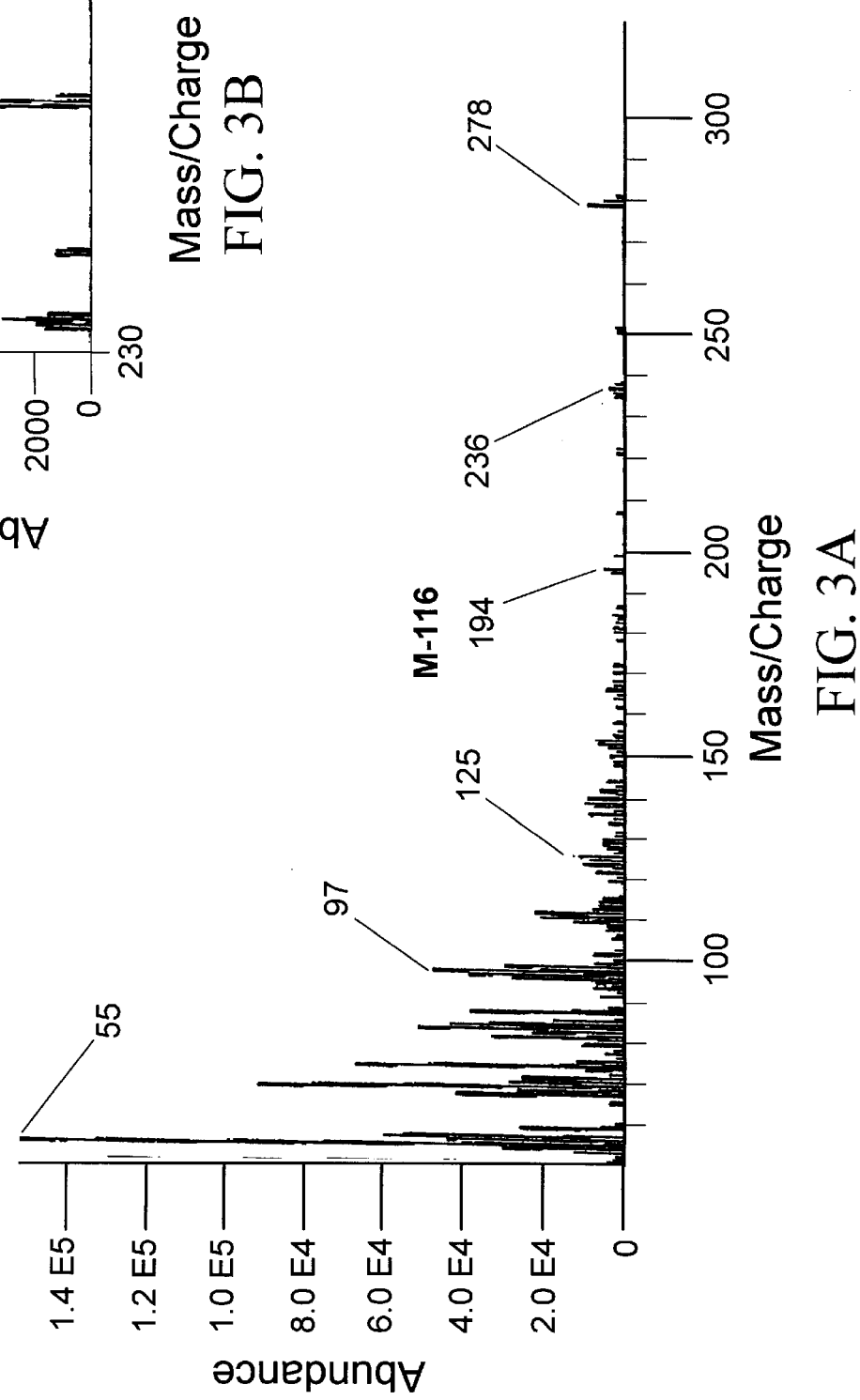
FIG. 3B
FIG. 3A

CYCLOPROPANE FATTY ACID EXPRESSION IN PLANTS

This application is a continuation of application Ser. No. 08/275,867, filed Jul. 15, 1994 now abandoned.

FIELD OF THE INVENTION

The present invention relates to plants containing the bacterial cyclopropane fatty acid synthase gene. Plants expressing this gene produce cyclopropane fatty acids. Expression of the gene in seeds will produce specialty oilseed crops. Cyclopropane fatty acids, and triacylglycerols containing these fatty acids, are useful in the lubrication and oleochemical industry. Additionally, the present invention includes chimeric genes expressible in plants and the transformed plants.

Vegetable oils are not only in the food industry, but increasingly in the chemical industry. Their utilization depends on the composition of the constituent fatty acids, which, in turn determines the chemical and physicochemical properties of the oil. It is desirable to modify the oil to meet industrial specifications. These specifications may be for the oil itself, or for fatty acids and derivatives derived from the oil. Modification of the oil may be accomplished by chemical means (fractionation, interesterification, hydrogenation, or other chemical derivatization), but genetic means (plant breeding, mutagenesis and genetic engineering) are increasingly being used to provide novel oil feedstocks. The use of genetic engineering allows the creation of novel oils which are unlikely to be achieved through breeding and mutagenesis. Higher plants transformed with genes encoding enzymes of either de novo fatty acid synthesis or fatty acid modification have been shown to produce novel fatty acid compositions. The enzymes are directed to the appropriate subcellular compartment (eg. plastids in the case of enzymes of de novo fatty acid synthesis) by targeting sequences. Progress towards oilseed modification has been reviewed by Ohlrogge, (1994), *Plant Physiology* 104:821–826.

*E. coli* and other bacteria have the ability to synthesize fatty acids containing a cyclopropane ring. The reaction is catalysed by the enzyme cyclopropane fatty acid synthase (also known as cyclopropane synthase or unsaturated phospholipid methyltransferase; E.C. 2.1.1.16) and involves the addition of a methylene group from S-adenosylmethionine across the double bond of phospholipid hexadecenoyl or octadecenoyl groups. Cyclopropane fatty acids (CFAs), such as dihydrosterculate (DHS) shown in the following formula, are characterized by a saturated 3-membered ring:

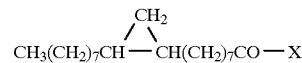

where X=OH for a free fatty acid, or an alcohol moiety for an ester. Physically, cyclopropane fatty acids have characteristics between those of saturated and monounsaturated fatty acids, and closer to the latter, whole the strained bond angles of the ring give them a unique chemistry, as described by Christie, W. W. (1970) in *Cyclopropane and Cyclopropane Fatty Acids. Topics in Lipid Chemistry* 1: 1–49. The cyclopropane fatty acid synthase gene in *E. coli* has been cloned and sequenced (Grogan et al., *J. Bacteriol.* 158:286–295 and Wang et al., *Biochemistry* 31: 11020–11028).

In gram negative bacteria, cyclopropane fatty acids occur in stationary phase membranes. The cyclopropane fatty acids produced by *E. coli* are synthesized on phospholipid substrates. In plants, unusual fatty aids are encountered primarily in seed oils. Certain fatty acid modifications, such as $\Delta 12$ desaturation or hydroxylation, occur on phospholipid substrates, and the fatty acids are then transferred to triacylglycerols. In a few plant species, cyclopropane fatty acids can reach high levels, ie, up to 40% in *Litchi chinensis*. Vickery et al., 1980, *J. Am. Oil Chem. Soc.* 57: 87–91; and Gaydou et al., 1993, *J. Ag. Food Chem.* 41: 886–890. It is more common to find cyclopropene fatty acids (the corresponding unsaturated cyclopropane fatty acids, particularly in the order Malvales (for example, as in the report by Bohannon and Kleiman, *Lipids* 13 (1978), 270–273), and a biosynthetic pathway through cyclopropane fatty acids was postulated by Yano et al., 1972, *Lipids* 7: 35–45. However, no in vitro measurement of cyclopropane fatty acid synthase activity has been reported in plant tissues to confirm the existence of this pathway. It is unknown if plants will express the bacterial cfa gene, if the corresponding messenger RNA will translate to active protein, and whether active bacterial cyclopropane fatty acid synthetase will cause the synthesis of cyclopropane fatty acid-phospholipids. Furthermore, it is unknown in plants where cyclopropane fatty acids do not occur normally whether these cyclopropane fatty acids will be channelled from phospholipids into triacylglycerol. Although the *E. coli* cyclopropane fatty acid synthase normally acts on phospholipids containing vaccenate (18:1$\Delta$11) and palmitoleate (16:1$\Delta$9), unsaturated fatty acid anxotrophs grown on oleate (18:1$\Delta$9) will accumulate the corresponding cyclopropane fatty acid, namely dihydrosterculate (DHS). Marinari et, al., 1974, *Biochemistry* 13: 1978–1983 and Ohlrogge et al., 1976, *Biochim. Biophys. Acta.* 431: 257–267. Phosphatidylethanolamine, phosphatidylglycerol and cardiolipin are effective substrates for purified *E. coli* cyclopropane fatty acid synthase. Phosphatidylcholine is unsatisfactory as a substrate for the *Clostridium butyricum* enzyme, Law, J. H. 1971, *Accts. Chem Res.* 4: 199–203.

When hydrogenated, cyclopropane fatty acids undergo ring opening which results in the formation of methyl-branched fatty acids. Methyl-branched fatty acids are useful in the formulation of lubricants. Kai, Y., 1982, *J. Am. Oil Chem. Soc.* 59: 300–305. A concentrate of methyl-branched fatty acids known as "isostearate", prepared from dimer acid production with subsequent hydrogenation and fractionation, is an article of commerce in the oleochemical industry and is used in applications as diverse as cosmetics and lubricant additives. Other ring-opening chemistries applied to cyclopropane fatty acids will produce novel oleochemical derivatives. Oils containing DHS as a replacement for oleate may maintain their good fluidity properties, but have enhanced oxidative stability, and hence be used in their own right as base fluids for lubricant applications.

The present invention relates to the unexpected discovery that plant tissues will express the bacterial cfa gene and the cyclopropane fatty acid synthase will catalyse the conversion of oleate to DHS in the plant cell.

SUMMARY OF THE INVENTION

Briefly, in accordance with the present invention, plant cells are transformed with a DNA sequence encoding a cyclopropane fatty acid synthase enzyme (cfa gene) in combination with a plant operable promoter and any other sequences necessary or desired for plant expression, i.e., polyadenylation sequences. The transformed plants produce cyclopropane fatty acids.

Of particular interest is the production in plants of dihydrosterculate (DHS) a compound useful for its application in the formulation of lubricants. The use of a seed specific promoter will enhance the production of this compound from the plant in an oilseed crop such as rape (Brassica sp.), sunflower (*Helianthus annus*) or soybean (*Glycine max*). Plants containing high levels of oleic acid in their seed oils would be best for obtaining maximum amounts of cyclopropane fatty acids. In addition, plants containing cis-vaccenate or palmitoleate would be suitable, as these acids would be converted to 11,12-methyleneoctadecanoate and 9,10-methylenebexadecanoate, respectively.

BRIEF DESCRIPTION OF THE DRAWINGS

FIG. 3 is a mass spectrum which shows fragments characteristic of DHS.

BRIEF DESCRIPTION OF THE SEQUENCES

Figure 1:
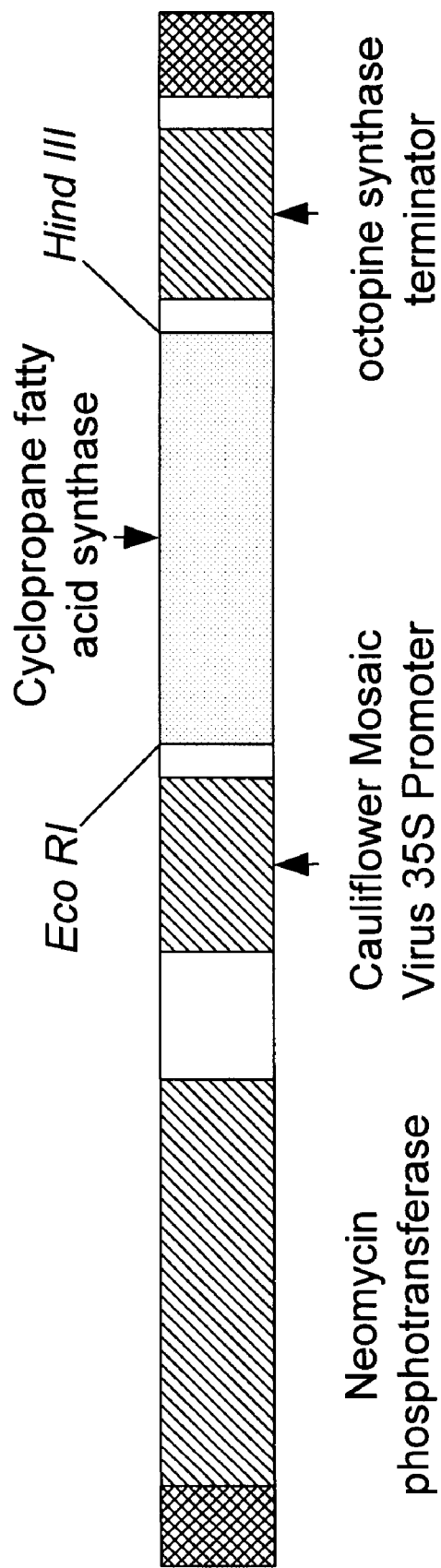
FIG. 1 is a diagram of the DNA construct employed in the examples.

SEQ ID NO. 1: represents the polynucleotide sequence of *E. coli* cyclopropane fatty acid synthase gene useful in accord with the principles of the subject invention.

DETAILED DESCRIPTION OF THE INVENTION

In practicing the present invention a bacterial cfa gene, combined with a plant operable promoter and any other desirable or necessary expression enhancing sequences, ie, termination sequences (polyadenylation sequences), is inserted into a transformation vector, and the plant cell employing standard transformation techniques. Once transformed, whole plants are regenerated which stably incorporate the cfa gene within their genome. The plants express the cfa gene. Expression can be constitutive or tissue specific. Since oil is produced from the seed of oilseed crops it is preferred to express the cfa gene under the control of a seed-specific promoter in oilseeds for maximum recovery of cyclopropane fatty acids for lubricant and other uses.

Any bacterial cfa gene can be employed in the present invention. As mentioned in the Background section, above, the cfa gene in *E. coli* has been cloned and sequenced and is preferred. Modifications can be made to the bacterial cfa gene as long as the biological activity of the resulting protein is not adversely effected. For example, different codons for the same amino acid residue may be substituted to enhance expression of the cfa gene in plants. One skilled in the art can readily determine condons preferred by a particular plant species by merely looking up codon bias in the literature such as GenBank.

Any plant operable promoter can be employed in the practice of the present invention. Seed specific promoters are preferred when high levels of cyclopropane fatty acids are desired in the seed oils. These promoters will have higher levels of expression and tissue specificity. Examples of such promoters are those derived from (i) genes for storage proteins which are deposited in the seed during maturation, examples of which include promoters isolated from phaseolin (Sengupta-Gopalan et al., 1985, *Proc. Natl. Acad. Sci. USA* 85: 3320–3324; Burow et al., 1992, *Plant J.* 527–548; and Bustos et al., 1991, *EMBO J.* 10: 1469–1479), helianthium (Nunberg et al., 1994, *Plant Cell* 6: 473) or napin (Stayton et al., 1991, *Aust. J. Plant Physiol.* 18: 507) genes, (ii) genes for inducible enzyme activities of lipid biosynthesis (examples include acyl carrier protein genes, as in reference WO 92/18634), and (iii) genes isolated and characterized merely by their tissue and temporal specificity (Bce4 gene in reference WO 91/13980). Other sequences that can affect expression of the cfa gene, such as, for example, leader sequences, targetting sequences and polyadenylation sequences, can also be included in the expression cassette.

Other desirable genes may also be inserted into the plant genome along with the cfa gene. Suitable genes include selectable markers (NPTII,PAT,BAR,DHFR, etc.); disease resistant genes; insect resistance genes, such as *Bacillus thuringiensis* (Bt) delta endotoxin genes; oil modification genes; and the like.

The present invention is not limited to a particular transformation process. Any of the known transformation methods can be used, such as for example, microinjection, polyethylene glycol, pricking, electroporation, silicon carbide whiskers, biolistics and Agrobacterium-mediated transformation and the like. All of these methods are well known to one of ordinary skill in the art. Additionally, once a plant cell is transformed, plants are regenerated therefrom employing regeneration techniques well known in the art.

The present invention is not limited to any particular plant or groups of plants. Any plant that can be transformed and regenerated, including monocots and dicots, can be included. Preferred plants include the oilseed crops, such as, rape (canola), sunflower, safflower, soybean, cotton palm, corn, olive, sesame, corn, peanuts, etc. When dihydrosterculate (DHS is the desired cyclopropane fatty acid then any plant that produces oleic acid can be employed.

In a preferred embodiment of the present invention, the production of DHS is accomplished by inserting a functional cfa gene into a plant species that produces oleic acid preferably a high levels, eg., high-oleic varieties of rape, peanut or sunflower containing over 70% oleic acid. An expression cassette would include in the 5' to 3' direction: a speed specific promoter sequence, the cyclopropane fatty acid synthase structural gene sequence and optionally a termination polyadenylation sequence. Once transformed the plant cell is regenerated into a fertile, morphologically normal plant (R-0),. The seeds of this plant can be collected and the DHS recovered therefrom, or the seed can be gown into plants (R-1) for seed production or for plant breeding purposes. When a crop is grown for DHS production the seeds are collected and the oil fraction is separated employing well known techniques. The DHS is readily isolated from the other oil components. The hydrogenation of DHS will produce methyl-branched fatty acids that can in turn be used in lubricant formulations.

The following examples illustrate the practice of the present invention but should not be construed to limit its scope.

EXAMPLE 1

The DNA sequence encoding the *E. coli* cfa gene (SEQ ID NO. 1) was combined with the CaMV 35S promoter and introduced into tobacco cells via *Agrobacterium tumefaciens* mediated transformation. The cyclopropane fatty acid synthase coding sequence was prepared by polymerase chain reaction (PCR) using a derivative of pG122 as a template. The 5' and 3' primers incorporated a Hind III and an Eco RI site respectively. The PCR product was incorporated into the EcoRV site of pBluescript KS-by blunt end ligation. A Hind III/Eco RI fragment was inserted into the polylinker of binary vector pGA748, a derivative of PGA643 in which the polylinker contains a unique Eco RI site (G. An.). *Agrobacterium tunefaciens* LBA4404 was transformed with the resulting pCP4 by electroporation. See FIG. 1 which shows the portion of pCP4 between the T-DNA borders.

Aliquots of *Nicotiana tabacum* liquid culture were wounded by repeated pipetting in the presence of 20 nM acetosyringone. Cells where then cocultivated for 3 days with *A. tumefacies* containing either PCp4 or pGA758 before the transfer to plates containing 500 ug/ml carbenicillin and 100ug/ml kanamycin. Resistant calli were transferred to fresh anitbiotic containing plates and analyzed for fatty acid composition.

Gas chromatography-mass spectrometry analysis of fatty acids from the transformed callus revealed the presence of the C-19 dihydrosterculate (DHS) cyclopropane fatty acid in 23 out of 30 isolates. Proportions of the DHS reached 3% in about half the isolates. The highest level of DHS was 9.9%. Analysis of more than one callus from the same line gave somewhat variable DHS levels possibly due to variations in size and density of the callus. The DHS occurred primarily in the phospholipid of the tobacco plant. As seen in Table 1 below, the DHS was present in triacylglycerols (TAGs) at a higher percentage level than the total transesterified lipid. Therefore DHS can be transferred from the phospholipid to TAG.

TABLE 1

| ISOLATE | % DHS in total lipid | % DHS in TAG | % TAG in Total Lipid |
|---|---|---|---|
| D1 | 1.8 | 4.3 | 5.6 |
| D3 | 2.8 | 8.2 | 4.3 |
| E7 | 8.3 | 12.0 | 6.7 |

Figure 2:
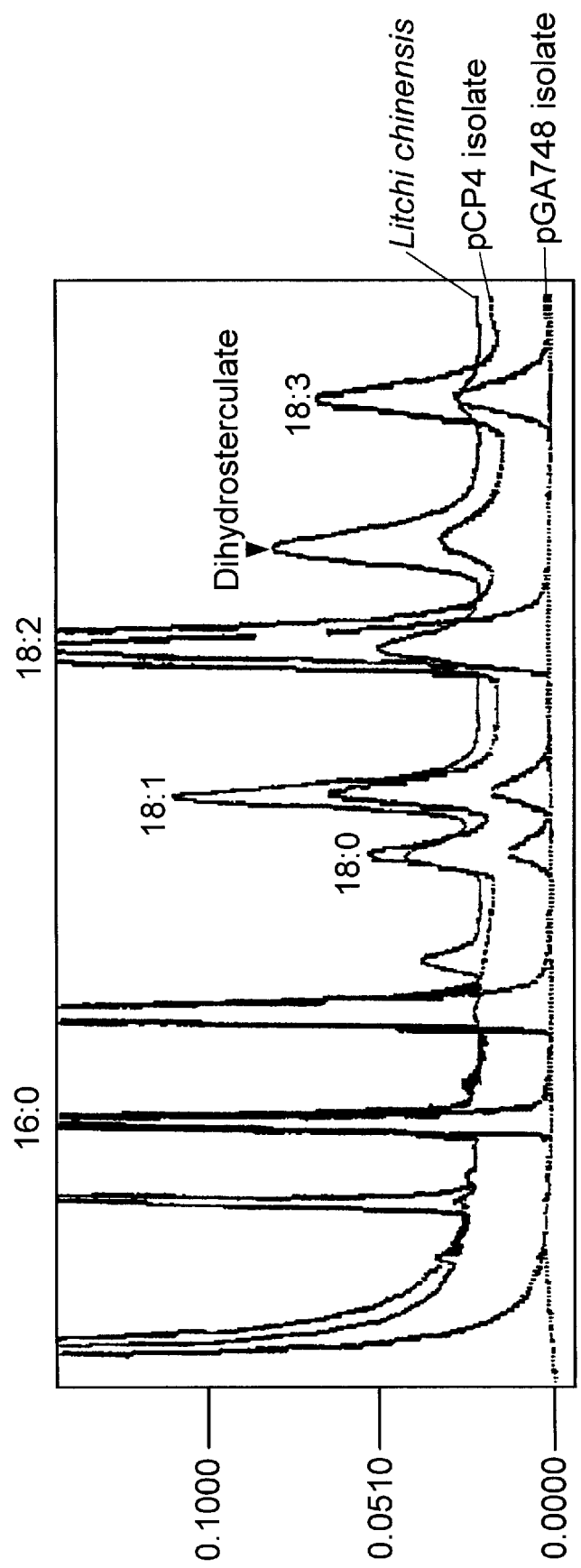
FIG. 2 is a chromatogram of the fatty acid methyl esters isolated from tissue of pCP4 transformant.

An isolate containing the cfa gene from pCP4 was compared by gas-liquid chromotography (glc) with *Litchi chinensis and a pGA*748 isolate (does not contain the cfa gene). Lipids were extracted with hexane/isopropanol (3:2) and transesterified with sodium methoxide. Fatty acid methyl esters were quantitated by flame ionization following glc on a 12 foot DEGS column. *Litchi chinensis* oil and hydrogenated *Sterculia foetida* oil were used as qualitative standards. See FIG. 2 for the results which indicate a peak in the pCP4 isolate that corresponds with DHS.

A mass spectrum of the DHS fatty acid methyl ester peak show fragments characteristic of a 19 carbon cyclopropane fatty acid. See FIG. 3. Gas chromatography-mass spectrometry marked are characteristic ions in the spectrum of methyl dihydrosterculate (MDHS). See Christie, et al, 1996, Lipids 1: 176–182. The ring position cannot be verified by this method.

EXAMPLE 2

Tobacco cells were transformed with the expression cassette disclosed in Example 1 employing the Agrobacterium leaf disc transformation method of Horsch et al., 1985, Science 227: 1229–31. Fatty acid methyl esters isolated from transformed plant tissue contain a peak comigrating with methyl DHS during gas chromatography. Table 2 below shows the percentages of the various fatty acids contained in the plants.

TABLE 2

| Fatty Acid | Sample Transformed with CFA Gene | | | | | | Vector only | | |
|---|---|---|---|---|---|---|---|---|---|
| | 1 | 2 | 3 | 4 | 5 | avg | A | B | avg |
| 16:0 | 14.2 | 11.7 | 13.5 | 16.1 | 14.0 | 13.9 | 14.0 | 10.6 | 12.3 |
| 16:1 | 1.5 | 2.0 | 1.6 | 1.1 | 1.5 | 1.5 | 1.1 | 1.5 | 1.3 |
| 18:0 + 16:3 | 2.7 | 6.4 | 5.0 | 2.0 | 6.2 | 4.5 | 7.1 | 8.2 | 7.7 |
| 18:1 | 3.2 | 2.2 | 2.3 | 1.4 | 2.0 | 2.2 | 1.9 | 1.0 | 1.4 |
| 18:2 | 12.7 | 13.7 | 15.4 | 9.2 | 12.8 | 12.8 | 11.4 | 7.9 | 9.7 |
| DHS | 2.1 | 0.9 | 1.2 | 2.5 | 1.2 | 1.6 | 0.0 | 0.0 | 0.0 |
| 18:3 | 63.6 | 63.1 | 61.0 | 67.7 | 62.3 | 63.5 | 64.5 | 70.8 | 67.6 |
| | 100.0 | 100.0 | 100.0 | 100.0 | 100.0 | 100.0 | 100.0 | 100.0 | 100.0 |

In similar operations various plants described herein transformed with bacterial CFA synthase genes produce cyclopropane fatty acids. The plant transformed, tobacco, can be defined as an oilseed since its seeds contain sufficient high levels of triacylglycerols as a percentage weigth of the see, greater than soybean, which is the premier oilseed crop (by volume) in the world today.

What I claim is:

1. A chimeric gene comprising:
   a. a plant operable promoter;
   b. a bacterial cyclopropane fatty acid synthase structural gene, and
   c. a polyadenylation sequence
wherein the chimeric gene is expressed under control of the plant operable promoter when inserted into a plant genome.

2. The chimeric gene of claim 1 wherein the promoter is CaMV35S promoter.

3. The chimeric gene of claim 1 wherein the structural gene is E. coli cyclopropane fatty acid synthase gene.

4. The chimeric gene of claim 1 wherein the promoter is a seed specific promoter.

5. The chimeric gene of claim 4 wherein the seed specific promoter is derived from a phaseolin, napin or acyl carrier protein gene.

6. A stably transformed plant cell comprising:
   a plant operable promoter,
   b. a bacterial cyclopropane fatty acid synthase structural gene, and
   a polyadenylation sequence
wherein cyclopropane fatty acid synthase is expressed under control of the plant operable promoter in the plant cell.

7. The cell of claim 6 wherein the promoter is CaMv 35S.

8. The cell of claim 6 wherein the structural gene is E. coli cyclopropane fatty acid synthase gene.

9. The cell of claim 6 wherein the plant operable promoter is a seed specific promoter.

10. The stably transformed plant cell of claim 9 wherein the seed specific promoter is derived from a phaseolin, napin or acyl carrier protein gene.

11. The cell of claim 10 wherein the structural gene is E. coli cyclopropane fatty acid synthase gene.

12. A method of producing cyclopropane fatty acid compounds which comprises:

a. stably transforming a plant cell with a bacterial cyclopropane fatty acid synthase gene that is functional in plants;

b. culturing the transformed plant cell;

c. regenerating a whole plant from the culture wherein the plant expresses the cyclopropane fatty acid synthese gene; and d. recovering cyclopropane fatty acid produced by the plant.

13. The method of claim 12 wherein the cyclopropane fatty acid synthase gene is a DNA sequence encoding *E. coli* cyclopropane fatty acid synthase.

14. The method of claim 12 wherein the plant cell is derived from an oilseed crop.

15. The method of claim 14 wherein the plant cell is selected from the group consisting of rape, sunflower, soybean, peanut, safflower, cotton, sesame, corn, olive and palm.

16. The method of 15 wherein the cyclopropane fatty acid compound is dihydrosterculate.

17. A method of producing dihydrosterculate comprising:

a. growing an oleic acid producing oilseed crop which has been stably transformed with a bacterial cyclopropane fatty acid synthase gene that is expressed in the seed;

b. harvesting the oilseed crop; and c. recovering the dihydrosterculate from the seed.

18. The method of claim 17 wherein the cyclopropane fatty acid synthase gene is *E. Coli* cyclopropane fatty acid synthase gene.

19. The method of claim 18 wherein the cyclopropane fatty acid synthase gene is driven by a phaseolin, napin or acyl carrier protein promoter.

20. The method of claim 17 wherein the oilseed crop is selected from the group consisting of rape, sunflower, safflower, soybean, sesame, peanut, cotton, corn and palm.

* * * * *

UNITED STATES PATENT AND TRADEMARK OFFICE
CERTIFICATE OF CORRECTION

PATENT NO. : 5,936,139
DATED : August 10, 1999
INVENTOR(S) : Katherine M. Schmid It is certified that error appears in the above-identified patent and that said Letters Patent is hereby corrected as shown below:

Abstract:
Line 1: "Pants" should read -- Plants --.

Column 1,
Line 63: "whole" should read -- while --.

Column 2,
Line 7: "aids" should read -- acids --;
Line 36: "anxotrophs" should read -- auxotrophs --.

Column 3,
Line 7: "sequences. The transformed plants produce" should read
-- sequences. The transformed cells are regenerated into whole plants where the cfa gene is expressed. The transformed plants produce --;
Line 22: "methylenebexadecanoate" should read -- methylenehexadecanoate --.

Column 4,
Line 20: "cfa" should read -- cyclopropane fatty acid --;
Line 54,: "a high" should read -- at high --.

Column 5,
Line 22: "tunefacies" should read -- tumefaciens --;
Line 28: "tumefacies" should read -- tumefaciens --.

Column 6,
Lines 28-31: "Gas chromatography-mass spectrometry marked are characteristic ions in the spectrum of methyl dihydrosterculste (MDHS)." should read -- Gas chromatography-mass spectrometry was performed on an HP5890 gas chromatograph with a 30m DB-23 column, linked to an HP5970 Mass Selective Detector. The molecular ion (m/z=310) and the fragments marked are characteristic ions in the spectrum of methyl dihydrosterculate (MDHS). --;
Table 2, column heading: "CFA" should read -- cfa --;
Line 65: "CFA" should read -- cyclopropane fatty acid --.

UNITED STATES PATENT AND TRADEMARK OFFICE
CERTIFICATE OF CORRECTION

PATENT NO. : 5,936,139
DATED : August 10, 1999
INVENTOR(S) : Katherine M. Schmid It is certified that error appears in the above-identified patent and that said Letters Patent is hereby corrected as shown below:

Column 7,
Line 57: "CaMV35S" should read -- CaMV 35S --.

Column 8,
Line 1: "see," should read -- seed, --;
Line 51: "a polydenylation" should read --c. a polydenylation --;
Line 54: "CaMv 35S" should read -- CaMV 35S --.

Column 9,
Line 8: "acid produced" should read -- acid compounds produced --

Signed and Sealed this

Fourteenth Day of August, 2001

*Attest:*

*Attesting Officer*

NICHOLAS P. GODICI
*Acting Director of the United States Patent and Trademark Office*

```
                        SEQUENCE LISTING

<160> NUMBER OF SEQ ID NOS: 1

<210> SEQ ID NO 1
<211> LENGTH: 1149
<212> TYPE: DNA
<213> ORGANISM: Escherichia coli

<400> SEQUENCE: 1
atgagttcat cgtgtataga agaagtcagt gtaccggatg acaactggta ccgtatcgcc      60
aacgaattac ttagccgtgc cggtatagcc attaacggtt ctgccccggc ggatattcgt     120
gtgaaaaacc ccgatttttt taaacgcgtt ctgcaagaag gctctttggg gttaggcgaa     180
agttatatgg atggctggtg ggaatgtgac cgactggata tgttttttag caaagtctta     240
cgcgcaggtc tcgagaacca actcccccat catttcaaag acacgctgcg tattgccggc     300
gctcgtctct tcaatctgca gagtaaaaaa cgtgcctgga tagtcggcaa agagcattac     360
gatttgggta atgacttgtt cagccgcatg cttgatccct tcatgcaata ttcctgcgct     420
tactggaaag atgccgataa tctggaatct gcccagcagg cgaagctcaa aatgatttgt     480
gaaaaattgc agttaaaacc agggatgcgc gtactggata ttggctgcgg ctggggcgga     540
ctggcacact acatggcatc taattatgac gtaagcgtgg tgggcgtcac catttctgcc     600
gaacagcaaa aaatggctca ggaacgctgt gaaggcctgg atgtcaccat tttgctgcaa     660
gattatcgtg acctgaacga ccagtttgat cgtattgttt ctgtggggat gttcgagcac     720
gtcggaccga aaaattacga tacctatttt gcggtggtgg atcgtaattt gaaaccggaa     780
ggcatattcc tgctccatac tatcggttcg aaaaaaaccg atctgaatgt tgatccctgg     840
attaataaat atattttcc gaacggttgc ctgccctctg tacgccagat tgctcagtcc     900
agcgaacccc actttgtgat ggaagactgg cataacttcg gtgctgatta cgatactacg     960
ttgatggcgt ggtatgaacg attcctcgcc gcatggccag aaattgcgga taactatagt    1020
gaacgcttta aacgaatgtt tacctattat ctgaatgcct gtgcaggtgc tttccgcgcc    1080
cgtgatattc agctctggca ggtcgtgttc tcacgcggtg ttgaaaacgg ccttcgagtg    1140
gctcgctaa                                                            1149
```